US00PP17792P2

(12) United States Plant Patent
Heil

(10) Patent No.: US PP17,792 P2
(45) Date of Patent: Jun. 12, 2007

(54) CARNATION PLANT NAMED 'CLASSICA'

(50) Latin Name: *Dianthus caryophyllus*
Varietal Denomination: Classica

(75) Inventor: Johan Edwin Heil, Aalsmeer (NL)

(73) Assignee: P. Kooÿ + Zonen B.V., Aalsmeer (NL)

( * ) Notice: Subject to any disclaimer, the term of this patent is extended or adjusted under 35 U.S.C. 154(b) by 181 days.

(21) Appl. No.: 11/073,465

(22) Filed: Mar. 5, 2005

(51) Int. Cl.
*A01H 5/00* (2006.01)

(52) U.S. Cl. ..... Plt./273

(58) Field of Classification Search ..... Plt./273, Plt./277

See application file for complete search history.

*Primary Examiner*—Kent Bell
(74) *Attorney, Agent, or Firm*—C. A. Whealy

(57) ABSTRACT

A new and distinct cultivar of Carnation plant named 'Classica', characterized by its compact, upright and rounded plant habit; freely basal branching habit; freely flowering habit; and red purple-colored flowers.

1 Drawing Sheet

Botanical designation: *Dianthus caryophyllus.*
Cultivar denomination: 'Classica'.

CROSS-REFERENCE TO RELATED APPLICATIONS

The present application is co-pending with the following related application (U.S. Plant patent application Ser. No. 11/073,466): Carnation Plant Named 'Cristal'; Johan Edwin Heil, applicant.

BACKGROUND OF THE INVENTION

The present invention relates to a new and distinct cultivar of potted Carnation plant, botanically known as *Dianthus caryophyllus* and hereinafter referred to by the cultivar name Classica.

The new Carnation is a product of a planned breeding program conducted by the Inventor in Aalsmeer, The Netherlands. The objective of the breeding program is to develop new compact Carnation cultivars suitable for container production with attractive flower coloration.

The new Carnation originated from a cross-pollination made by the Inventor of the *Dianthus caryophyllus* cultivar Sunflor Campari, disclosed in U.S. Plant Pat. No. 12,740, as the female, or seed, parent with the *Dianthus caryophyllus* cultivar Rubato, not patented, as the male, or pollen, parent. The cultivar Classica was discovered and selected by the Inventor as a flowering plant within the progeny of the stated cross-pollination in a controlled environment in Aalsmeer, The Netherlands, in 2000.

Asexual reproduction of the new cultivar by terminal cuttings in Aalsmeer, The Netherlands, has shown that the unique features of this new Carnation are stable and reproduced true to type in successive generations of asexual reproduction.

SUMMARY OF THE INVENTION

The cultivar Classica has not been observed under all possible environmental conditions. The phenotype may vary somewhat with variations in environment such as temperature and light intensity without, however, any variance in genotype.

The following traits have been repeatedly observed and are determined to be the unique characteristics of 'Classica'. These characteristics in combination distinguish 'Classica' as a new and distinct cultivar:

1. Compact, upright and rounded plant habit.
2. Freely basal branching habit.
3. Freely flowering habit.
4. Red purple-colored flowers.

Compared to plants of the female parent, the cultivar Sunflor Campari, plants of the new Carnation are more compact, have larger flowers and differ in flower coloration. Compared to plants of the male parent, the cultivar Rubato, plants of the new Carnation are easier to grow under low temperature conditions.

Plants of the new Carnation can be compared to plants of the cultivar Pink Surprise, not patented. In side-by-side comparisons conducted in Aalsmeer, The Netherlands, plants of the new Carnation and the cultivar Pink Surprise differed in the following characteristics:

1. Plants of the new Carnation had broader leaves than plants of the cultivar Pink Surprise.
2. Plants of the new Carnation were more freely flowering than plants of the cultivar Pink Surprise.
3. Plants of the new Carnation had larger flowers with more petals per flower than plants of the cultivar Pink Surprise.
4. Flower color of plants of the new Carnation was slightly darker than flower color of plants of the cultivar Pink Surprise.

Plants of the new Carnation can also be compared to plants of the cultivar Cristal, disclosed in U.S. Plant patent application Ser. No. 11/073,466. In side-by-side comparisons conducted in Aalsmeer, The Netherlands, plants of the new Carnation and the cultivar Cristal differed in the following characteristics:

1. Plants of the new Carnation had broader leaves than plants of the cultivar Cristal.

2. Plants of the new Carnation were more freely flowering than plants of the cultivar Cristal.
3. Flowers of plants of the new Carnation were not as fragrant as flowers of plants of the cultivar Cristal.
4. Plants of the new Carnation and the cultivar Cristal differed in flower coloration.

BRIEF DESCRIPTION OF THE PHOTOGRAPH

The accompanying colored photograph illustrates the overall appearance of the new Carnation, showing the colors as true as it is reasonably possible to obtain in colored reproductions of this type. Colors in the photograph may differ slightly from the color values cited in the detailed botanical description which accurately describe the colors of the new Carnation. The photograph comprises a top perspective view of a typical flowering plant of 'Classica' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown in Aalsmeer, The Netherlands in a glass-covered greenhouse. During the production of the plants, day temperatures were about 15° C. and night temperatures were about 8° C. Rooted young plants were planted in 10-cm containers and pinched once. The photographs and the description were taken about five months after planting.

Botanical classification: *Dianthus caryophyllus* cultivar Classica.

Parentage:

*Female, or seed, parent.*—*Dianthus caryophyllus* cultivar Sunflor Campari, disclosed in U.S. Plant Pat. No. 12,740.

*Male, or pollen, parent.*—*Dianthus caryophyllus* cultivar Rubato, not patented.

Propagation:

*Type.*—By cuttings.

*Time to initiate roots, summer.*—About 8 days at 25° C.

*Time to initiate roots, winter.*—About 13 days at 18° C.

*Time to produce a rooted young plant, summer.*—About 20 days at 25° C.

*Time to produce a rooted young plant, winter.*—About 30 days at 18° C.

*Root description.*—Fine, fibrous.

*Rooting habit.*—Freely branching.

Plant description:

*Plant habit.*—Compact, upright and rounded plant habit.

*Growth habit.*—Freely basal branching; about six lateral branches per plant. Moderately vigorous.

*Plant height.*—About 17 cm.

*Plant width.*—About 17 cm.

*Lateral branch description.*—Length: About 10 cm. Diameter: About 2.5 mm. Internode length: About 2 mm. Aspect: Upright. Strength: Strong. Texture: Glabrous; smooth. Color: 145C.

*Foliage description.*—Arrangement: Leaves opposite; simple; symmetrical; abundant; sessile and decurrent. Length: About 10 cm. Width: About 9 mm. Shape: Linear. Apex: Acute. Margin: Entire. Texture, upper and lower surfaces: Glabrous; smooth. Venation pattern: Parallel, linear. Color: Developing and fully expanded foliage, upper surface: 137A; venation, 137B. Developing and fully expanded foliage, lower surface: 137B; venation, 137A.

Flower description:

*Appearance.*—Rotate flowers that face mostly upright. Freely flowering habit, about six to ten open flowers and flower buds per lateral branch.

*Flowering response.*—Plants flower during the summer in The Netherlands; during this period, flowering is continuous.

*Postproduction longevity.*—Flowers last about one week on the plant. Flowers persistent.

*Fragrance.*—Slight; clove-like.

*Flower size.*—Diameter: About 4 cm. Depth (height): About 3.5 cm.

*Flower buds.*—Length: About 1.8 cm. Diameter: About 9 mm. Shape: Ovoid. Color: 146B.

*Petals.*—Quantity/arrangement: About 35 per flower in numerous whorls. Length: About 3.3 cm. Width: About 1.6 cm. Shape: Flabellate. Apex: Rounded, praemorse. Base: Attenuate. Margin: Serrate. Texture, upper and lower surfaces: Smooth, glabrous. Color: When opening, upper surface: 67A. When opening, lower surface: 67C. Fully opened, upper surface: 67C. Fully opened, lower surface: 68B.

*Sepals.*—Quantity/arrangement: Five per flower fused into a calyx tube. Calyx length: About 2 cm. Calyx diameter: About 1.1 cm. Shape: Elliptic. Apex: Acute. Texture, upper and lower surfaces: Smooth, glabrous. Color, upper surface: 146B. Color, lower surface: 139C.

*Peduncles.*—Length: About 1.5 mm. Diameter: About 1 mm. Aspect: Upright. Strength: Moderately strong. Texture: Smooth; glabrous. Color: 145C.

*Reproductive organs.*—Androecium: Stamen number: About four. Filament color: 155D. Anther length: Less than 1 mm. Anther shape: Roughly oblong. Anther color: Close to 155D. Pollen: Scarce. Gynoecium: Pistil quantity: Two. Style length: About 2 cm. Style color: 155D. Ovary color: 145A.

*Seed.*—Length: About 3 mm. Diameter: About 2 mm. Color: 200A.

Disease/pest resistance: Plants of the new Carnation have not been observed to be resistant to pathogens nor pests common to Carnation.

It is claimed:

1. A new and distinct cultivar of Carnation plant named 'Classica', as illustrated and described.

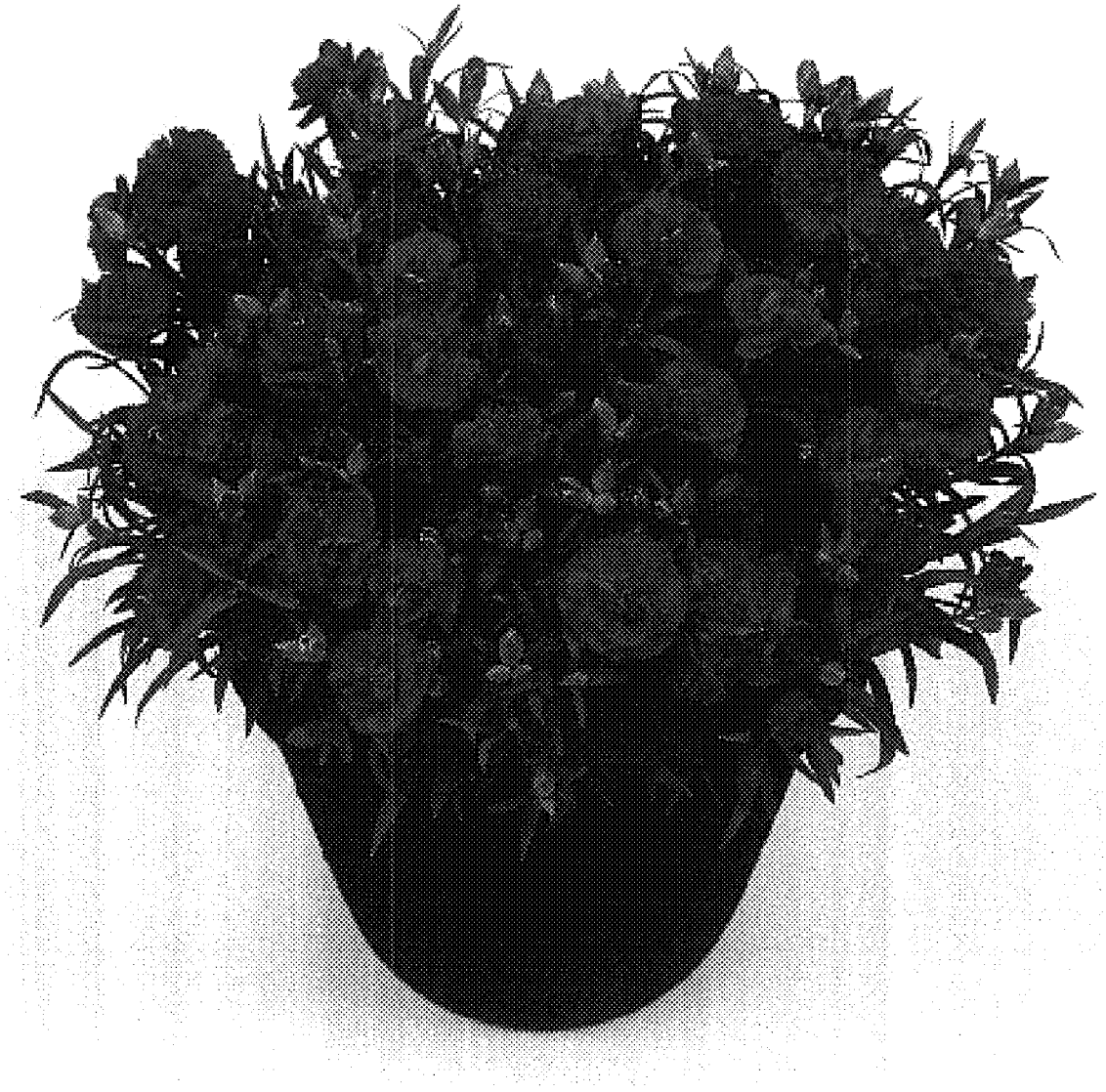

* * * * *